United States Patent [19]

Kwon et al.

[11] 4,446,428

[45] May 1, 1984

[54] MAGNETIC RESONANCE CELL

[75] Inventors: Tae M. Kwon, Thousand Oaks; Charles H. Volk, Newbury Park, both of Calif.

[73] Assignee: Litton Systems, Inc., Beverly Hills, Calif.

[21] Appl. No.: 307,996

[22] Filed: Oct. 2, 1981

[51] Int. Cl.$^3$ .............................................. G01R 33/08
[52] U.S. Cl. .................................... 324/304; 324/301
[58] Field of Search ................ 324/300, 301, 302, 304

[56] References Cited

U.S. PATENT DOCUMENTS

| | | | |
|---|---|---|---|
| 3,252,081 | 5/1966 | Ruddock et al. | 324/304 |
| 3,267,360 | 8/1966 | Dehmelt | 324/304 |
| 3,381,214 | 4/1968 | Exworthy | 324/301 |
| 3,500,176 | 3/1970 | Kastler et al. | 324/304 |
| 4,157,495 | 6/1979 | Grover | 324/302 |

Primary Examiner—Michael J. Tokar
Attorney, Agent, or Firm—Gerald L. Cline

[57] ABSTRACT

There is disclosed a nuclear magnetic alignment device for use in a nuclear magnetic resonance gyroscope and the like. One embodiment includes a container for gas having a layer of rubidium hydride on its inner surface. The container comprising a spherical portion and a tip portion, is rotationally symmetric about an axis of symmetry. Enclosed within the container is a nuclear moment gas having a nuclear electric quadrupole moment, such as xenon-131, and an optically pumpable substance, such as rubidium. A portion of the rubidium is a vapor. The remainder is a condensed pellet which is deposited in the tip of the container such that the pellet is also rotationally symmetric about the axis of symmetry of the container. A layer of rubidium hydride is deposited on the inner surface of the container. The device further includes means for orienting the symmetry axis of the container at an angle to an applied magnetic field such that the relaxation time constant of the aligned nuclear moment gas is substantially at a maximum.

44 Claims, 3 Drawing Figures

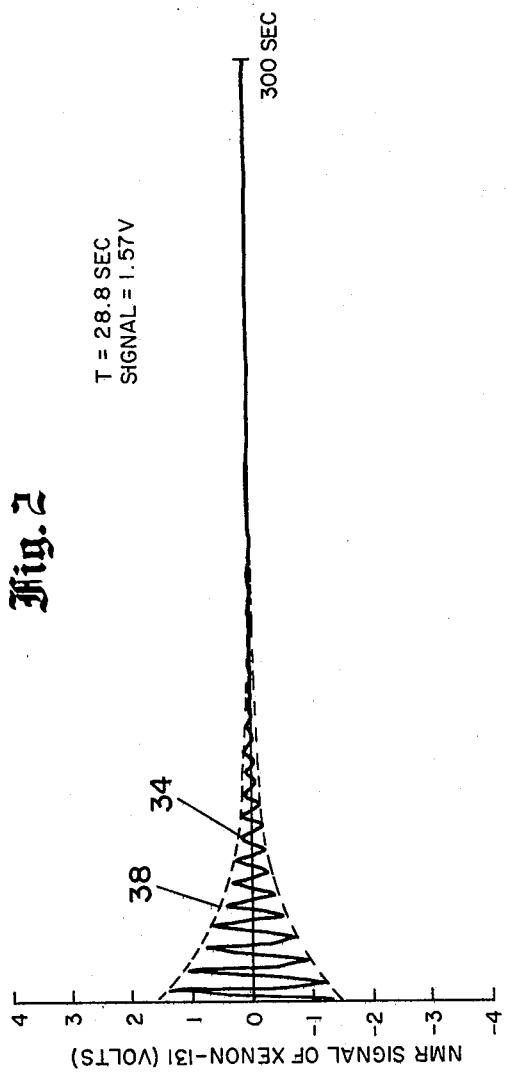
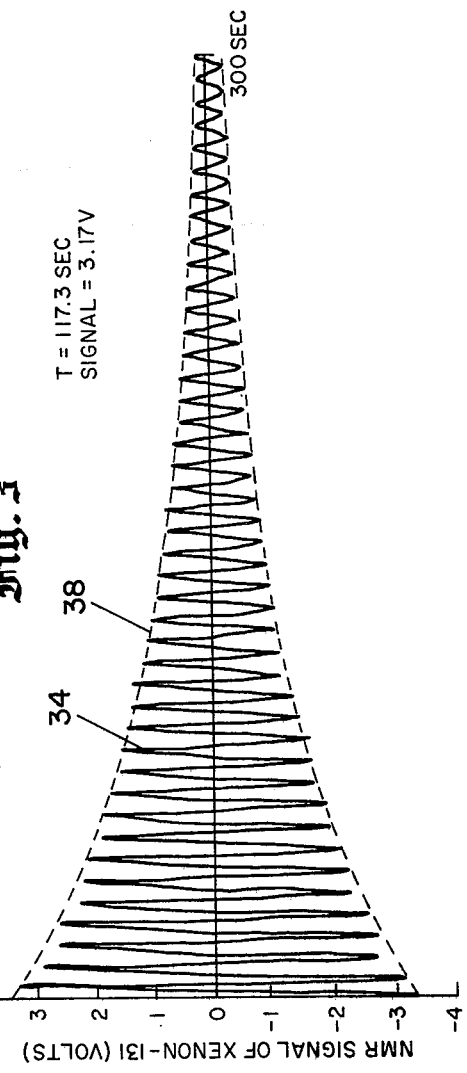

MAGNETIC RESONANCE CELL

TECHNICAL FIELD

This invention relates generally to the creation and detection of atomic and nuclear magnetic resonance. More particularly, this invention relates to magnetic resonance devices having aligned magnetic moment gases contained in a cell.

BACKGROUND ART

The present invention is directed to a magnetic resonance device with a gas container having its rotationally symmetric axis oriented at a given angle to the magnetic field, the container enclosing at least one magnetic moment gas having a nuclear electric quadrupole moment. The container also has an alkali metal hydride coating on the inner surface of the cell. Although the hydride coating is included and claimed here as part of the preferred embodiment, it is also the subject of a separate patent application, GCD 80-27-A, filed by T. M. Kwon and W. P. Debley, concurrently with the present application.

Magnetic resonance phenomena are well understood by those of ordinary skill in the art and a variety of its practical applications in the science and engineering fields are readily available. For the purposes of this discussion, magnetic resonance includes both atomic magnetic resonance and nuclear magnetic resonance.

One particular and important application of the invention to be described is to a nuclear magnetic resonance (hereinafter refered to as NMR) angular rate sensor or gyroscope. U.S. Pat. No. 4,157,495, hereby incorporated by reference into this document, discloses a NMR gyroscope that operates on the principle of sensing inertial angular rotation rate or angular displacement about a sensitive axis of the device as a shift in the Larmor precession frequency or phase, respectively, of one or more isotopes that possess nuclear magnetic moments.

The gyroscope is composed of an angular rotation sensor and associated electronics. The principal elements of the sensor are a light source, an NMR cell, a photodetector, a set of magnetic shields and a set of magnetic field coils. The principal elements of the electronics are signal processing circuits for extracting the Larmor precession frequency and phase information as well as circuits for generating and controlling various magnetic fields, both steady and varying sinusoidally with time, that are necessary for the proper operation of the device.

The NMR cell is mounted within a set of magnetic shields in order to attenuate external magnetic fields to acceptable low levels. Magnetic field coils are used to apply very uniform magnetic fields to the NMR cell. Both a steady field and an ac carrier field are applied along the sensitive axis of the device and AC feedback fields are applied along one of the transverse axes. The DC magnetic fields along both transverse axes are controlled to be substantially zero. The NMR cell contains a single alkali metal vapor, such as rubidium, together with two isotopes of one or more noble gases, such as krypton-83, and xenon-129, or xenon-131. One or more buffer gases such as helium and nitrogen may also be contained in the cell.

The NMR cell is illuminated by a beam of circularly polarized light that originates from a source such as a rubidium lamp and which passes through the cell at an angle with respect to the steady magnetic field. Absorption of some of this light causes the atomic magnetic moments of the rubidium atoms to be partly aligned in the direction of the steady magnetic field. This alignment is partly transferred to the nuclear magnetic moments of the noble gases, and these moments are caused to precess about the direction of the steady magnetic field, which in turn creates magnetic fields that rotate at the respective Larmor precession frequencies of the two noble gases. These rotating fields modulate the precessional motions of the rubidium magnetic moments, which in turn produce corresponding modulations of the transmitted light, thereby making it possible to optically detect the Larmor precession frequencies of the two noble gases.

The modulations of the light intensity are converted into electrical signals by a photodetector, and these signals are then electronically demodulated and filtered to provide signals at the Larmor precession frequencies of the two noble gases. The difference between the two precession frequencies is used to accurately control the steady magnetic field so that is constant. One of the noble gas precession frequencies is subtracted from a precision reference frequency. The resulting difference frequency is a measure of the angular rotation rate of the gyroscope. The magnitude of an individual nuclear magnetic moment is extremely small and the natural equilibrium condition is one in which a nearly random orientation of moments exists in an ensemble of atoms. Techniques must be used to orient a significant fraction of these magnetic moments in a single direction so that a macroscopic magnetic moment, and consequently a measureable signal, will be produced.

The aligned magnetic moments of the alkali metal atoms and of the atoms of both noble gases are subject to relaxation mechanisms which cause their alignments to decay exponentially with time towards their natural equilibrium condition of random orientation. Each system of moments is characterized by a relaxation time constant which depends on the kinds and quantities of all other constituents and upon the total environment in the NMR cell. The steady state fractional alignment of each system of moments is a function of both the pumping rate and the relaxation time for the system, with larger fractional alignments, hence larger signal amplitudes, being achieved when the relaxation times are also long.

Accordingly, a number of prior art techniques exist to achieve longer relaxation times. In one of the techniques, a suitable amount of a buffer gas such as helium or nitrogen is also contained in the cell in order to reduce the relaxation effects due to interactions of the magnetic moments with the walls of the cell. In another technique, particular isotopes of particular noble gases are chosen as the nuclear magnetic moment gases specifically for their long relaxation times. However, a problem still exists in that certain, otherwise desirable magnetic moment gases have relaxation times too short to provide a practical device.

In an article by D. S. Bayles, I. A. Greenwood, and J. H. Simpson in published report entitled, "Noise Sources in NMR Oscillators and Relaxation Phenomena in Optically-Pumped Mercury Isotopes", *Final Scientific Report*, Air Force Office of Scientific Research, 1976, Report No. ADA033737 from the Defense Technical Information Center, it was disclosed that the relaxation time constant of the vapor of mercury-201, a species having a nuclear electric quadrupole moment, is dependent on the particular angle of orientation of the axis of a cylindrically symmetric NMR cell to the externally applied magnetic field. The angle between the cell axis and the magnetic field which yielded the maximum relaxation time constant was termed the "magic angle", a term which will be used herein. Bayles et al determined that for mercury-201, the magic angle occured at $\cos^{-1}(\frac{1}{3})^{\frac{1}{2}}$ or approximately 55 degrees.

C. H. Volk, J. G. Mark, and B. C. Grover disclose in an article in *Physical Review A*, Volume 20, pps. 2381–2389, December, 1979, that this angle-dependent effect was observed for krypton-83, a noble gas also having a nuclear electric quadrupole moment. The magic angle was found experimentally to be an undetermined function of the spatial distribution of the reservoir of rubidium metal spread over the cell. Because of this undetermined dependence of magic angle on distribution of the rubidium metal, the magic angle for a given cell must be empirically determined by a time consuming trial and error approach in which the relaxation time constant is measured at many different angles of cell orientation.

SUMMARY OF THE INVENTION

Accordingly, it is an object of the present invention to provide a magnetic alignment device in which the aligned magnetic moments of a gas enclosed within a container have an increased relaxation time.

This and other objects and advantages are accomplished in a magnetic alignment device comprising a container for gas, at least one nuclear magnetic moment gas having a nuclear electric quadrupole moment enclosed within the container, and means for maintaining a substantial proportion of the electric field gradients rotationally symmetric about an axis of symmetry, the electric field gradients being experienced when the gas atoms collide with the container. The invention further comprises means for applying a steady magnetic field to the container and means for orienting the container so that the rotational axis of symmetry of the electric field gradients is at an angle to the magnetic field such that the relaxation time constant of the aligned nuclear moment gas is substantially at a maximum.

In one particular embodiment of the invention, the nuclear moment gas is xenon-131. The means for maintaining the axis of symmetry of the electric field gradients includes shaping the container with a spherical portion and a tip portion so that its inner surface is substantially rotationally symmetric about an axis of symmetry. The container also encloses an optically pumpable substance such as rubidium. A portion of the rubidium is a vapor. The remainder is a condensed pellet which is deposited in the tip of the container such that the pellet is rotationally symmetric about the axis of symmetry of the container. A layer of rubidium hydride is deposited on the inner surface of the container in order to predictably produce a magic angle of 55°.

BRIEF DESCRIPTION OF THE DRAWINGS

These and other objects, advantages, and features will become more fully apparent from the following detailed description of the invention when considered in conjunction with the accompanying drawings.

FIG. 2 shows the relaxation time of xenon-131 contained in a prior art nuclear magnetic resonance cell.

FIG. 3 shows the relaxation time of xenon-131 in a nuclear magnetic resonance cell constructed in accordance with one embodiment of the present invention.

DETAILED DESCRIPTION OF THE DRAWING

Figure 1:
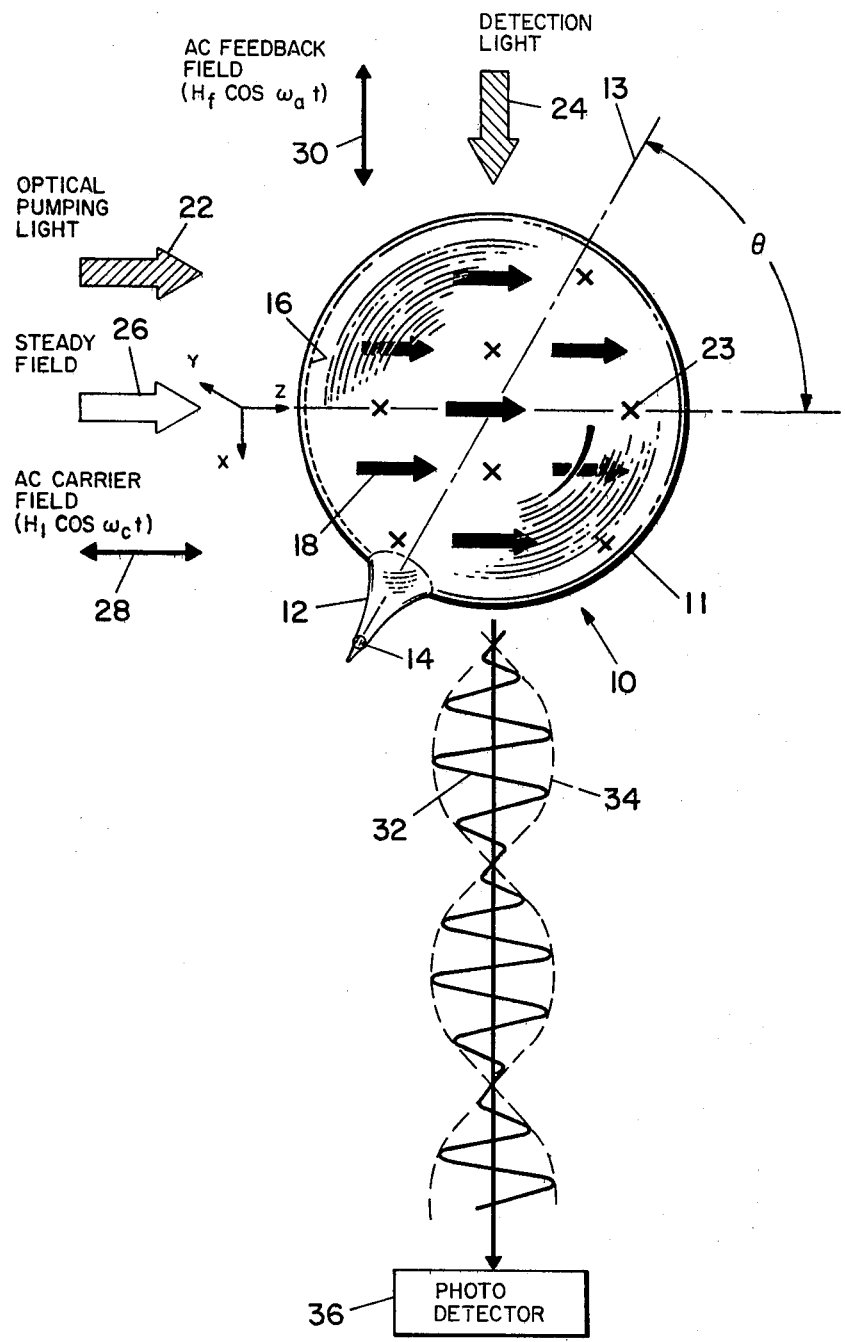
FIG. 1 is a conceptual diagram, adapted from FIG. 3 of U.S. Pat. No. 4,157,495, illustrating the operation of an NMR gyro having an NMR cell built in accordance with one embodiment of the present invention.

FIG. 1 is a conceptual diagram illustrating for each of the noble gases the processes of optical pumping and of modulation of the intensity of the light that is transmitted through the NMR cell 10.

The NMR cell 10 is a sealed, optically transparent container for gas which has a shape which is rotationally symmetric about an axis of symmetry 13. In a preferred embodiment, cell 10 includes a spherical portion 11 and a tip portion 12.

The cell 10 is suitably of Pyrex glass and has a volume of approximately one milliliter. The cell encloses at least one magnetic moment gas, such as xenon-131, having a nuclear electric quadrupole moment. In an illustrative embodiment, the cell contains a small quantity of isotopically enriched rubidium-87 metal, 0.1 Torr xenon-129, 0.4 Torr xenon-131, and a combination of buffer gases consisting of about 10 Torr nitrogen and 100 Torr helium. The cell 10 is filled through tip 12 which is then sealed off as shown.

Some of the rubidium is in the form of a pellet 14 deposited in the tip 12 while the rest is in the form of a vapor. The rubidium pellet 14 serves as a reservoir necessary to replenish the portion of rubidium vapor which gradually and inavoidably disappears from the interior of the cell.

In accordance with one aspect of the invention, the pellet 14 is disposed within tip 12 such that the pellet is substantially rotationally symmetric to the axis 13. In the specific embodiment of FIG. 1, this symmetry is achieved by having the tip 12 located on axis 13 thereby causing the pellet 14 to settle on axis 13. This is in contrast to the prior art magnetic resonance cells which use rubidium in an essentially uncontrolled spatial distribution over the inner surfaces of the cells.

The cell is mounted in a temperature controlled oven (not shown) and maintained at a temperature of approximately 80 degrees C., at which temperature rubidium is vaporized from pellet 14 in a quantity sufficient to absorb a substantial fraction of the pumping light entering the cell 10.

In further accordance with the invention, the axis 13 of cell 10 is oriented to the steady magnetic field 26 at approximately the magic angle $\theta$ where $\theta$ is defined by the expression $$\theta = \cos^{-1}(\tfrac{1}{3})^{\frac{1}{2}} \approx 55°$$

It should be understood that the magic angle is actually a cone angle in that the axis 13 can be oriented at the magic angle in any aribitrary direction about the steady field 26 to thereby sweep out an imaginary cone having its axis along the field 26. Furthermore, the magic angle is independent of the directional sense of the steady magnetic field 26. Thus, a 180° reversal of magnetic field 26 leaves the magic angle undisturbed.

The orientation and symmetry of the cell described above is in accordance with the discovery that the relaxation time of a magnetic moment gas, having a nuclear electric quadrupole moment, such as xenon-131, is increased if the inner surface of the container 10 and pellet 14 each have a co-linear rotational axis of symmetry, such as axis 13, which is aligned at the magic angle to the magnetic field.

Reasoning based on the theory of quantum mechanics indicates that an aligned atom having a nuclear electric quadrupole moment, in particular with a total electronic spin of zero, such as possessed by xenon-131, krypton-83 and mercury-201, is relaxed by the electric field gradients which it experiences during collisions of the atom with the walls of the container. Theory further indicates that when these electric field gradients are rotationally symmetric about an axis which is substantially at the magic angle to the applied magnetic field, then the relaxation time is at a maximum. Such rotational symmetry is provided by a cell whose inner surface has a rotational axis of symmetry such as exists for the container 10 and pellet 14 of FIG. 1.

A layer 16 of rubidium hybride is deposited on the inner walls of container 10. As will be discussed, it has been discovered that such a film significantly increases the relaxation time constant of the xenon-131 magnetic moments. The increase is additive to the increase gained by the technique for orientation of the axis of symmetry of the NMR cell to the magic angle described previously. In contrast to this magic angle technique which works only for gases with nuclear electric quadrupole moments, the alkali hydride coating increases the relaxation time of magnetic moment gases with or without a nuclear electric quadrupole moment.

As was noted previously, such a coating, although it is part of the preferred embodiment of FIG. 1, and also part of the invention claimed herein, is also the subject of a separate patent application GCD 80-27A.

Because the processes of optical pumping and of modulation of intensity of the light transmitted through cell 10 are so similar for each of the two noble gases, they are illustrated and described for only one of the two noble gases. The circularly polarized light at a preselected wavelength which rubidium absorbs, is from a rubidium vapor lamp. The light which enters the NMR cell 10 through the sperical portion 11 has a component 22 traveling along the z-axis which is referred to as optical pumping light, and a component 24 traveling along the x-axis, which is referred to as detection light. Through the interactions of the optical pumping light 22 and the steady magnetic field 26, the rubidium atoms 18 have their magnetic moments aligned preferentially in the z-direction. By inter-atomic collisions, this magnetic moment alignment is transferred from the rubidium atoms 18 to the noble gas nuclei 23.

A sinsusoidal ac feedback magnetic field 30 that is matched in frequency and phase to the Larmor precession frequency of the collective magnet moment of the noble gas nuclei 23 is applied in the x-direction and serves to torque the magnetic moment of these nuclei to the x-y plane. This component of noble gas nuclear magnetic moment then precesses in the x-y plane at the noble gas Larmor precession frequency $\omega_a$ about the steady magnetic field 26. This precessing nuclear magnetic moment component creates a nuclear precession magnetic field of strenght $h_a$ that rotates in the x-y plane and which therefore has component in the y-direction that is equal to ($h_a \cos \omega_a t$).

The detection light 24 interacts with the rubidium atoms 18 which are under the influence of the steady magnetic field 26, a superimposed AC carrier magnetic field 28, and the y-component of the nuclear precession field $h_a$. This interaction causes the intensity of the x-component of the transmitted light 32 to be modulated at the carrier frequency $\omega_a$, with a modulation envelope 34 at the nuclear precession frequency $\omega_a$. These light modulations are then converted into electrical signals by the photodetector 36. The electrical signals may be used by an electronic circuit to create signals which are measures of angular velocity of the gyro as in U.S. Pat. No. 4,157,495.

In order to demonstrate the invention, the relaxation times of aligned nuclear magnetic moments of xenon-131 were experimentally measured for a number of cells made in the same batch, the cells being identical except that some were made with and the others made without a coating of rubidium hydride. The experimental apparatus was similar to that of FIG. 1 except that it was operated not as a gyroscope, but rather to specifically measure the relaxation time of xenon-131 by measuring the effective magnetic field $h_a$ generated by the aligned xenon-131. This well known mode of operation is thoroughly discussed in articles by C. Cohen-Tannoudji, J. Dupont-Roc, S. Haroch, and F. Laloe, in *Physical Review Letters*, Volume 22, page 758, 1969; and by the same authors in *Review de Physique Appliquee*, Volume 5, page 102, 1970; and by C. H. Volk, T. M. Kwon, and J. G. Mark in *Physical Review A*, Volume 21, page 1549, 1980.

For sake of completeness of the disclosure, the particular experimental procedures will now be described. The rubidium vapor is optically pumped by illuminating the cell with circularly polarized light from a rubidium discharge lamp at the $D_1$ rubidium spectral line.

In the presence of the pumping light, a 2 milligauss field was applied along the z-axis, for 10 minutes a time in which a significant fraction of the noble gas magnetic moments are aligned along the z-axis by spin exchange collisions with the optically oriented vapor. The Z-field is then switched to zero while a precessional magnetic field of approximately 350 microgauss is applied along the y-axis. An ac magnetic field is simultaneously applied along the x-axis for the purpose of detecting the precessional magnetic field generated by the aligned xenon nuclear magnetic moments.

The y-axis field mentioned above defines the axis about which the cell axis is oriented to yield a magic angle, i.e., the angle at which the maximum relaxation time constant occurs. This maximum was found to occur when the cell axis 13 was oriented at the magic angle of approximately 55° to the y-axis, in excellent agreement with the theoretical value of 55°. The relaxation time constant was not significantly decreased by changing the cell angle by approximately plus and minus 5° away from 55°.

FIGS. 2 and 3 show the typical results of these experiments. In both figures the horizontal axis represents time and the vertical axis represents the response of the silicon photodetector 36 to the x-component of the transmitted light 32. The sinusoidal signal 34 is the modulation envelope of the x-component of the transmitted light. The envelope 38 of the signal 34 yields the relaxation time constant. As shown in FIG. 2, the cell without the rubidium hybrid coating has a relaxation time of 28.8 seconds. This is significantly shorter than for the coated cell of FIG. 3 which has a relaxation time constant of 117.3 seconds. The signal amplitudes of FIGS. 2 and 3 are 1.57 volts and 3.17 volts, respectively, thereby indicating an improvement in signal to noise ratio of over a factor 2 for the coated cell with respect to the uncoated cell. This increased signal is a direct result of the increased relaxation time.

With the axis 13 of container 10 set at the magic angle, it was found that relaxation of the aligned xenon-131 took place in a very short time when the rubidium reservoir was distributed non-uniformly over the inner surface of container 10, as in the prior art, rather than spatially concentrated as in the pellet 14 in tip 12. In fact, this prior art distribution caused complete relaxation to take place in a few periods of the precession signal 34, a time far too short for a practical device. When the rubidium was concentrated into the tip 12 as the pellet 14, the relaxation time was increased to the times shown in FIGS. 2 and 3.

With the pellet 14 located on axis 13, the magic angle occurred much more often at the theoretically predicted 55 degrees in those cells having a layer of rubidium hydride than for those without the layer. For example, in a typical batch of 20 cells having the layer of rubidium hydride, approximately 85% had their magic angle substantially at 55 degrees. This was in contrast to another batch of 100 cells made without a layer of rubidium hydride in which only 15% had magic angles at substantially 55 degrees.

A further advantage of combining the rubidium hydride coating with the symmetrical cell is the fact that those cells having a magic angle of 55 degrees exhibited a larger precessional signal 34 than cells having some other magic angle.

Although the reasons for the beneficial effects of rubidium hydride coatings on a nuclear magnetic resonance cell are not completely understood, theoretical work has been carried out which gives the following highly tentative physical picture. The rubidium hydride covers microscopic impurities non-uniformly located on the inner surface of the container that, unless coated, give rise to strong microscopic electric field gradients at the walls. These gradients produce strong relaxation forces upon the aligned moments of the gas.

In addition, the non-uniform location of the impurities on the wall decreases the symmetry of the field gradients on the inner surface of the cell which, in the case of nuclear electric quadrupole moment gases, is required to reliably produce a magic angle at 55 degrees.

It thus follows that the relaxation time increase is caused, at least in part, by a reduction in field gradients effected by the coating. By reducing the magnitude of the effects of the non-uniformly distributed wall impurities, the coating also produces a greater symmetry of field gradients so that cells with nuclear electric quadrupole moment gases are more likely to have magic angles at 55°.

A further reason for these beneficial effects is believed to be that the coating modifies the adsorption energy of the cell walls so as to reduce the sticking time, the time period which an atom colliding with the cell wall remains on the wall prior to rebounding away. This advantageously decreases the time during which the field gradients can act on the colliding atom, thereby decreasing the relaxation effects.

In one particularly suitable method of producing the layer 16 of rubidium hydride on the inner surface of container 10 shown in FIG. 1, the glass container 10 is first connected at the tip 12 to a vacuum gas filling system. After evacuation, the cell 10 is filled with the species and in the amounts previously described with the addition of approximately 10 Torr of hydrogen gas. The rubidium is added in an amount in excess of a stoichmetric mixture with respect to the hydrogen. The substances can be added in any convenient order. The cell 10 is then sealed, removed from the vacuum gas filling system and then maintained at an elevated temperature for a time period sufficient for the hydrogen and rubidium to react to produce a ribidium hydride coating on the inner surface of the container. The presence of the coating manifests itself by a clearly visible milky color on the cell walls. The temperature at which the cell is maintained is sufficiently high to form rubidium hydride on the inner walls of cell 10 within a time period short enough to be practical. The temperature is sufficiently low so to maintain an unreacted portion of the rubidium metal within the cell. In one embodiment of the method, the temperature was maintained at approximately 85° C. for approximately 7 days. In other embodiments the temperature can be maintained in the range from 70° C. to 90° C. from between 4 to 14 days.

Practical temperatures can range from about 70° C. to about 250° C. At much below the lower temperature, the reaction takes too long to be practical. Much above the higher temperature, it has been determined that the unreacted rubidium metal disappears, probably because of diffusion into or through the cell walls or of a reaction with the cell walls. An additional short coming of such a higher temperature is that impurities are driven off the cell walls, resulting in contamination of the gas mixture.

Insofar as known, the method of manufacturing a coating of rubidium hydride described above is novel.

During the heating period, the unreached rubidium metal is vaporized and re-deposited all over the walls. After the heating is completed, the spatially dispersed rubidium is re-vaporized and condensed as the pellet 14 positioned in the tip 12 by the well known technique of gently heating the cell 10 with a flame while holding the tip 12 in cool water so as to maintain the top cooler than the cell walls.

One prior art method for making rubidium hydride consists of heating a mixture of rubidium and hydride to a temperature range between 400 and 600 degrees C. As described above, such a high temperature range would cause problems of making rubidium hydride coatings in a closed system. However it could be used to make the coating in cells which were then cooled down prior to adding excess rubidium and other gases.

Another known method of manufacturing rubidium hydride consists of reacting a mixture of rubidium and hydrogen by subjecting the mixture to a high intensity light source, such as a laser, at the wavelength corresponding to the resonance radiation line of rubidium. Although such a method might produce useable coatings, it is more expensive than the method used for the invention because of the need for a high power laser.

Although the invention has been described with reference to a particular embodiment, numerous modifications will be obvious to those schooled in the art. Therefore it is intended that such modifications shall lie within the scope of the invention as claimed in the following claims.

For example, a known type of NMR gyroscope uses mercury-201 as an optically pumpable substance but does not have a pellet, i.e., a reservoir of condensed material. In such a device it is apparent that the relaxation time can be increased in accordance with the invention by using a cell having a rotationally symmetric axis oriented at the magic angle, but that the container need not have a tip portion since there is no condensed reservoir.

As another example, it is expected that the beneficial effects of a layer of rubidium hydride are shared by other alkali metal hydrides including hydrides of cesium, potassium, sodium and lithium.

The benefit of a rotationally symmetric cell oriented to the magic angle extends to most, if not all, magnetic moment gases having a nuclear electric quadrupole moment with a total electronic spin of zero, including xenon-131, neon-21, krypton-85, krypton-83, and mercury-201.

The scope of the invention extends to gas containers for magnetic moment gases which are made from materials other than glass, including quartz, fused silica, sapphire, and similar smooth walled containers.

What is claimed is:

1. A nuclear magnetic moment alignment device comprising:
    (a) a container for gas, said container having its inner surface substantially rotationally symmetric about an axis of symmetry;
    (b) means for applying a steady magnetic field to said container;
    (c) at least one nuclear magnetic moment gas selected from the group consisting of xenon-131, neon-21, krypton-85, and krypton-83, said magnetic moment gas being capable of being aligned in a predetermined direction to said magnetic field, said gas being enclosed in said container;
    (d) means for orienting said container so that said axis of symmetry of said container is at an angle to said magnetic field so as to be capable of causing the relaxation time constant of the nuclear magnetic moment of said at least one nuclear moment gas to be substantially at a maximum.

2. The device of claim 1 further comprising at least one vapor of optically pumpable substance capable of transferring the alignment of its magnetic moment to the magnetic moment of said nuclear moment gas, said vapor enclosed within said container.

3. The device of claim 2 further comprising a supply of said optically pumpable substance in a non-vapor state, said supply constituting a reservoir enclosed within said container, said supply being disposed in a rotationally symmetric arrangement about said axis of symmetry of said container.

4. The device of claims 1, 2, or 3 wherein a layer of alkali metal hydride is disposed on the inner surface of said container, where the alkali metal is selected from the group consisting of cesium, lithium, potassium, sodium, and rubidium.

5. The device of claims 1, 2 or 3 wherein a layer of alkali metal hydride is disposed on the inner surface of said container where the alkali metal is selected from the group consisting of cesium, potassium, sodium, and rubidium.

6. The device of claims 1, 2, or 3 wherein a layer of rubidium hydride is disposed on the inner surface of said container.

7. The device of claims 1, 2 or 3 wherein said at least one nuclear magnetic moment gas is xenon-131.

8. The device of claim 1 wherein said angle is from approximately 50 degrees to 60 degrees.

9. The device of claim 8 wherein said angle is approximately 55 degrees and, is substantially given by $\theta$, where $$\theta = \cos^{-1}(\tfrac{1}{3})^{\tfrac{1}{2}}$$

10. A nuclear moment alignment device for use in a nuclear magnetic resonance gyroscope and the like, comprising;
    (a) a container for gas, said container having a substantially rotationally symmetric axis of symmetry;
    (b) at least one nuclear moment gas having a nuclear electric quadrupole moment gas selected from the group consisting of xenon-131, neon-21, krypton-85, and krypton-83, said gas contained within said cell;
    (c) at least one vapor from an optically pumpable substance capable of transferring the alignment of its magnetic moment to the magnetic moment of said nuclear moment gas;
    (d) means for applying a steady magnetic field to said container;
    (e) means for illuminating said cell with pumping light capable of partially aligning the magnetic moments of said at least one optically pumpable substance along the direction of said magnetic field;
    (f) a supply of said optically pumpable substance in a non-vapor state, said supply constituting a reservoir enclosed within said container;
    (g) means for disposing said supply of optically pumpable substance in a rotationally symmetric arrangement about said axis of symmetry of said container; and
    (h) means for orienting said axis of symmetry at an angle to said magnetic field so as to be capable of causing the relaxation time of said magnetic moment of said nuclear moment gas to be substantially at a maximum.

11. The device of claim 10 further comprising a layer of alkali metal hydride on the inner surface of said container, where the alkali metal is selected from the group consisting of cesium, lithium, potassium, sodium, and rubidium.

12. The device of claim 10 further comprising a layer of an alkali metal hydride on the inner surface of said container, where the alkali metal is selected from the group consisting of cesium, sodium, and rubidium.

13. The device of claim 10 further comprising a layer of rubidium hydride on the inner surface of said container.

14. The device of any one of claims 10 through 13 wherein the optically pumpable substance is an alkali metal selected from the group consisting of cesium, sodium and rubidium.

15. The device of any one of claims 10 through 13 wherein said optically pumpable substance is rubidium.

16. The device of claim 15 wherein said at least one nuclear magnetic moment gas is xenon-131.

17. The device of any one of claims 10 through 13 wherein said angle is from approximately 50 degrees to approximately 60 degrees.

18. The device of claim 17 wherein said angle $\theta$ is approximately 55 degrees where $$\theta = \cos^{-1}(\tfrac{1}{3})^{\tfrac{1}{2}}$$

19. The device of any one of claims 10 through 13 wherein said means for disposing said reservoir of optically pumpable substance in a rotationally symmetric arrangement comprises a tip portion of said cell which is rotationally symmetric to said axis of symmetry, and in which said reservoir is deposited.

20. A method of increasing the relaxation time constant of aligned nuclear magnetic moments of a magnetic moment gas used in a nuclear magnetic alignment device of the type wherein a container for gas encloses at least one nuclear moment gas selected from the group comprising xenon-131, neon-21, krypton-85 and krypton-83 and at least one vapor of an optically pumpable substance capable of transferring the alignment of its magnetic moment to the magnetic moment of said nuclear moment gas, and said container is illuminated with pumping light capable of partially aligning the magnetic moments of said at least one pumpable substance along a steady magnetic field applied to said container, comprising:
 (a) accumulating within said container a supply of said optically pumpable substance in a non-vapor state, said supply constituting a reservoir:
 (b) fabricating said container into a shape which is substantially rotationally symmetric about an axis of symmetry;
 (c) disposing said supply of said substance so that it is rotationally symmetric about said axis of symmetry of said container; and
 (d) orienting said container at an angle to said magnetic field such that the relaxation time constant of said aligned at least one nuclear moment gas is substantially at a maximum.

21. The method of claim 20 further comprising coating the inner surface of said container with a layer of an alkali metal hydride where the alkali metal is selected from the group consisting of cesium, potassium, sodium, lithium, and rubidium.

22. The method of claim 20 further comprising coating the inner surface of said container with an alkali metal hydride where the alkali metal is selected from the group consisting of cesium, potassium, sodium, and rubidium.

23. The method of claim 20 further comprising coating the inner surface of said container with rubidium hydride.

24. The method of any one of claims 20 through 23 wherein the optically pumpable substance is an alkali metal selected from the group consisting of cesium, sodium, or rubidium.

25. The method of any one of claims 20 through 23 wherein said optically pumpable substance is rubidium.

26. The method of any one of claims 20 through 23 wherein said angle $\theta$ is from approximately 50 degrees to approximately 60 degrees.

27. The methods of either of claims 20 through 23 wherein said angle $\theta$ is from approximately 50 degrees to approximately 60 degrees.

28. The method of claim 27 wherein said angle is approximately 55 degrees, where $$\theta = \cos^{-1}(\tfrac{1}{3})^{\tfrac{1}{2}}$$

29. A nuclear moment alignment device for use in a nuclear magnetic resonance gyroscope comprising;
 (a) a container for gas, said container including a tip portion, said container having a substantially rotationally symmetric axis of symmetry passing through said tip portion of said cell;
 (b) means for applying a steady magnetic field to said container;
 (c) a gas of xenon-131 contained within said cell, the magnetic moment of said gas being capable of being aligned in a predetermined direction to said magnetic field;
 (d) a vapor of rubidium contained within said cell;
 (e) means for illuminating said cell with pumping light capable of partially aligning the magnetic moments of said rubidium along the direction of said magnetic field;
 (f) a reservoir of rubidium in a non-vapor state, said rubidium disposed in said tip portion such that said axis of symmetry passes through said reservoir of rubidium; and
 (g) means for orienting said axis of symmetry at an angle $\theta$ to said magnetic fields so as to be capable of causing the relaxation time of said nuclear magnetic moment of said gas of Xenon-131 to be substantially at a maximum.

30. The device of claim 29 further comprising a layer of rubidium hydride on inner surface of said container.

31. The device of claim 29 wherein said angle $\theta$ is from approximately 50 degrees to approximately 60 degrees.

32. The device of claim 31 wherein said angle $\theta$ is approximately 55 degrees, where $$\theta = \cos^{-1}(\tfrac{1}{3})^{\tfrac{1}{2}}$$

33. A method of improving the performance of a nuclear magnetic moment alignment device comprising:
 (a) fabricating container for gas, said container having its inner surface substantially rotationally symmetric about an axis of symmetry;
 (b) applying a steady magnetic field to said container;
 (c) enclosing within said container at least one nuclear magnetic moment gas selected from the group consisting of xenon-131, neon-21, krypton-85, and krypton-83, said magnetic moment gas being capable of being aligned in a predetermined direction to said magnetic field;
 (d) orienting said container so that said axis of symmetry of said container is at an angle to said magnetic field so as to be capable of causing the relaxation time constant of the nuclear magnetic moment of said at least one nuclear moment gas to be substantially at a maximum.

34. The method of claim 33 further comprising coating the inner surface of said container with alkali metal hydride where the alkali metal is selected from the group consisting of cesium, potassisum, sodium, lithium, and rubidium.

35. The method of claim 33 further comprising coating the inner surface of said container with an alkali metal hydride where the alkali metal is selected from the group consisting of cesium, potassium, sodium, and rubidium.

36. The method of claim 33 further comprising coating the inner surface of said container with rubidium hydride.

37. The method of any one of claims 43 or 34 through 41 wherein the optically pumpable substance is rubidium.

38. The method of any one of claims 33 or 34 through 36 wherein said angle is from approximately 50 degrees to approximately 60 degrees.

39. The method of claim 37 wherein said angle is from approximately 50 degrees to approximately 60 degrees.

40. The method of claim 38 wherein said angle $\theta$ is approximately 55 degrees, where $$\theta = \cos^{-1}(\tfrac{1}{3})^{\frac{1}{2}}$$

41. The method of claim 39 wherein said angle $\theta$ is approximately 55 degrees, where $$\theta = \cos^{-1}(\tfrac{1}{3})^{\frac{1}{2}}$$

42. The method of claim 33 further comprising inserting within said container at least one vapor of optically pumpable substance capable of transferring the alignment of its magnetic moment to the magnetic moment of said nuclear moment gas.

43. The method of claim 42 further comprising accumulating within said container a supply of said optically pumpable substance in a non-vapor state, said supply constituting a reservoir enclosed within said container, said supply being disposed in a rotationally symmetric arrangement about said axis of symmetry of said container.

44. The device of claim 2 or claim 3 wherein said optically pumpable substance is rubidium.

* * * * *